United States Patent [19]

Dodge

[11] 4,086,925
[45] May 2, 1978

[54] MEDICAL DRAINAGE DEVICE WITH ADJUSTABLE SUPPORTING STRAP

[75] Inventor: Larry H. Dodge, St. Charles, Mo.

[73] Assignee: Sherwood Medical Industries Inc., St. Louis, Mo.

[21] Appl. No.: 731,598

[22] Filed: Oct. 12, 1976

[51] Int. Cl.² ............................................. A61J 1/00
[52] U.S. Cl. .................................. 128/272; 128/275; 128/DIG. 24; 224/45 C
[58] Field of Search ............... 128/272, 295, 2 F, 275, 128/DIG. 5, DIG. 24; 206/438; 150/33; 224/46 R, 45 H, 55, 58, 45 C, 45 P, 49

[56] References Cited

U.S. PATENT DOCUMENTS

| 2,542,246 | 2/1951 | Grosz | 224/46 R X |
| 3,699,815 | 10/1972 | Holbrook | 128/2 F X |
| 4,036,231 | 7/1977 | Dodge et al. | 128/DIG. 5 X |

Primary Examiner—Robert W. Michell
Assistant Examiner—Michael H. Thaler
Attorney, Agent, or Firm—S. N. Garber; W. R. O'Meara

[57] ABSTRACT

A thoracic drainage device including a fluid collection chamber for receiving drainage fluid from the pleural cavity of a patient is provided with a strap capable of being used to conveniently support the drainage device in various ways. The upper and lower ends of the drainage device are provided with openings for receiving the strap in each of a plurality of different device supporting conditions. The strap can be adjusted so as to be useable as a shoulder strap, a hand-held strap, a strap for hanging the drainage device from a bed rail or other support, or in other arrangements. The strap can be arranged to provide a relatively short support without having unused portions dangling from the device.

21 Claims, 7 Drawing Figures

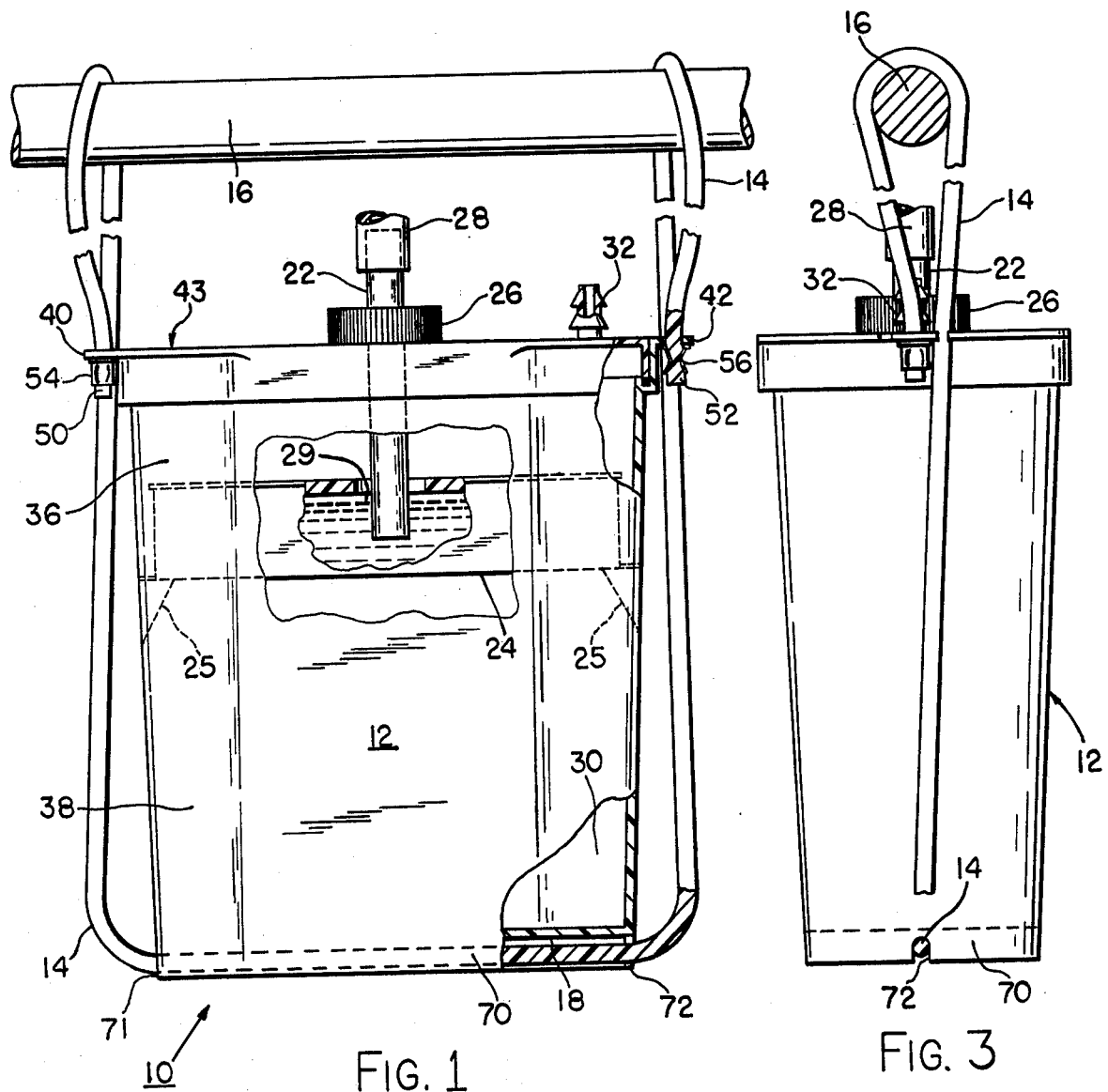

MEDICAL DRAINAGE DEVICE WITH ADJUSTABLE SUPPORTING STRAP

BACKGROUND OF THE INVENTION

This invention relates to medical drainage devices and more particularly to a body fluid drainage device having a strap capable of supporting the device in various manners.

In body fluid drainage systems, such as a thoracic drainage system, a catheter is positioned in the pleural cavity of the patient and connected to a fluid drainage container or bottle. In the well-known "one-bottle" system, a bottle vented to atmosphere is provided with an initial amount of liquid and an inlet drainage tube that extends to a point near the bottom of the bottle and below the level of the liquid to provide a liquid seal between the atmosphere and the pleural cavity. One of the disadvantages of such an arrangement is that, as the level of liquid drainage rises above the lower end of the tube, the force necessary to expel fluid from the pleural cavity increases due to the increasing pressure head above the tube outlet. In order to avoid this increasing liquid head, the well-known "two-bottle" system employing a second bottle as a series liquid seal between the atmosphere or a source of vacuum and the first bottle may be used. In the latter arrangement, the drainage tube in the collection chamber is near the top of the bottle and is not immersed in the liquid.

The "two-bottle" arrangement is, of course, more complicated and requires more space. When such bottles are glass bottles, they are generally placed on the floor or other flat support because of the shape of the bottles and because they are relatively heavy. Such bottles are sometimes formed with a neck and jug-like finger hole on the neck for carrying the bottle. However, when supported by the finger hole, the bottle tilts because the hole is not on the vertical axis of the bottle. Thus, glass bottles are heavy, require considerable space, and the manner of positioning and supporting glass bottles of this type is practically limited generally to placing them on a flat support such as the floor of a room.

SUMMARY OF THE INVENTION

It is an object of the present invention to provide a medical drainage device having improved means for supporting the device in various selected ways.

Another object is to provide a body fluid drainage device which is compact, highly effective in operation, relatively light in weight, and has improved means for supporting the device in several selected ways.

In accordance with one form of the present invention, a drainage collection device is provided with a supporting strap having opposite end portions connected to the device. The upper portion of the device is provided with a plurality of spaced slots for receiving the strap when the strap is in various selected device-supporting arrangements.

These, as well as other objects and advantages of the present invention will become apparent from the following detailed description and accompanying drawings.

BRIEF DESCRIPTION OF THE DRAWINGS

FIG. 1 is a front elevational view of a thoracic drainage device in accordance with a preferred embodiment of the invention and shown with the drainage device suspended from a rail;

FIG. 2 is a top plan view of the drainage device of FIG. 1;

FIG. 3 is a side elevational view of the drainage device of FIG. 1;

DESCRIPTION OF THE PREFERRED EMBODIMENT

Figure 4:
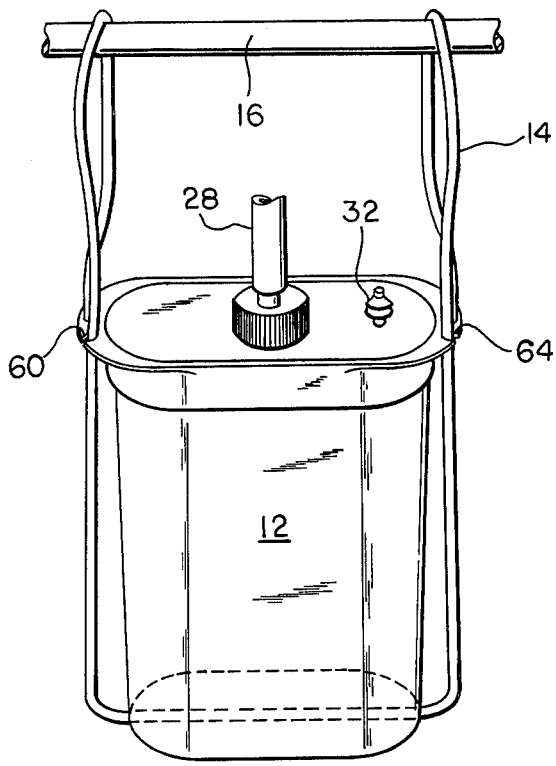
FIG. 4 is a perspective view of the drainage device of FIG. 1, on a reduced scale, with the strap supporting the drainage device in a somewhat modified manner.

Referring now to the drawings, and particularly to FIGS. 1-3, there is shown a medical thoracic drainage device 10 including a container 12 for receiving body fluid from a patient, and a strap 14 for supporting the container in several different manners. The container is shown in FIGS. 1, 3 and 4 as being supported from a rod or rail 16, such as a bed rail.

Container 12 is closed at the lower end by an integral bottom wall 18 and at the top by a cover or lid 20, as seen in FIG. 2 a fluid inlet conduit or tube 22 extends through the cover 20 and into a liquid seal chamber 24 mounted in the upper portion of the container 12 such as on fixed wall abutments 25. A removable threaded cap 26 on a threaded container neck (not shown) sealingly secures the tube 22 in place on cover 20. The upper end of tube 22 is sealingly received within one end of a fluid conduit or tube 28 which is adapted to be connected to a catheter which, in turn, is adapted for insertion into the pleural cavity of a patient to be drained of fluid. The liquid seal chamber 24 is initially filled with a liquid 29, such as a saline solution. The tube 22 extends below the level of the liquid in chamber 24 to provide a liquid seal for the pleural cavity of the patient. The upper end of the seal chamber 24 is open about the tube 22 so that drainage liquid from the pleural cavity will overflow the seal chamber and flow over the top of the seal chamber and down the sided into a body fluid collection chamber 30 located below the seal chamber. Because the drainage liquid overflows chamber 24, there is a substantially constant head above the lower end of tube 22 so that the force necessary to expel fluid from the patient remains substantially constant.

Any gas flowing from the pleural cavity will bubble up through the liquid in the seal chamber 24, pass out the upper open end of the seal chamber, and out a vent passage indicated at 32. The vent passage 32 connects the interior of the container 12 above the liquid seal chamber 24 either with the atmosphere, as shown, or with a vacuum source, as desired or required. Where it is desired to employ a vacuum, the vent passage 32 is connected by a tube (not shown) to a source of vacuum and preferably to a source of regulated vacuum for the protection of the patient. For a further detailed description and operation of thoracic drainage devices of this type, reference may be had to U.S. application Ser. No.

619,109, filed Oct. 2, 1975, and U.S. application Ser. No. 633,873, filed Nov. 20, 1975, now Pat. No. 4,036,231, both of which are assigned to the assignees of the present application.

The container 12 is generally oblong in cross-section and has an upper half portion 36 and a lower half portion 38. The upper portion 36 has flanges 40 and 42 at its opposite sides which extend outwardly from the container. These flanges are shown as integral extensions of the upper end 43 of the container.

A pair of holes 44 and 46 are respectively provided in flanges 40 and 42 that are on the lonitudinal center, that is, these holes are intersected by a lateral axis indicated at 48 in FIG. 2. The strap 14 has its opposite ends, indicated at 50 and 52, passing through the holes 44 and 46. The size of these holes and the diameter of strap 14 are preferably made to effect a friction fit. A pair of retaining members shown as crimped eyelets 54 and 56 are fixed to the free ends 50 and 52 of the strap below the flanges 40 and 42, the eyelets being larger than the holes 44 and 46 to prevent the strap ends from becoming disconnected from the container 12.

Flange 40 is provided with a pair of grooves 58 and 60 on opposite sides of hole 44, and flange 42 is provided with a pair of similar grooves 62 and 64 on opposite sides of the hole 46. Each of the four grooves is identical and includes a generally circular hole 66 located inwardly from the periphery of the flange in which it is disposed, and an entrance slot 68 open to the periphery of the flange and extending from the flange periphery inwardly and connecting with the associated hole 66. The strap 14 can be inserted, side wall first, into the hole 66 by moving it through the entrance slot 68. For example, the longitudinal axis of the strap 14 can be parallel with the axis of the hole 66 when the strap is moved from the periphery of the flange into the hole. Each of the four holes 66 has a size or diameter smaller than the diameter of strap 14 to provide a friction fit. Each of the four entrance slots preferably has a portion narrower than the diameter of the strap so that the strap will not inadvertently slide out during normal handling of the device but can be manually moved through the slot.

The lower half portion 38 of the container 12, as best seen in FIGS. 1 and 3, has a peripheral wall or skirt 70 extending downwardly beyond the bottom wall 18 of the collection chamber 30 a distance at least as great as the diameter of the strap 14, and preferably greater. A pair of grooves 71 and 72 are respectively located in the wall 70 and intersected by an axis parallel to the axis 48 in FIG. 2. Grooves 71 and 72 extend to the bottom of the container to receive the strap 14 and such that the strap can extend vertically along the sides and along the bottom of the container as shown in FIGS. 3 and 4. In this way, the strap, in effect, is shortened at the top and without having a dangling portion of the strap. Thus, an effectively shortened strap is obtained for hanging the deivce 12 such as from the bed rail 16. In this construction, the strap can extend along the bottom of the container as shown and the container can be placed in a standing position on a flat surface without interference from the strap.

In FIGS. 1 and 3, the container 12 is shown hanging from the bed rail with the strap 14 extending from its ends, over the bed rail 16, down through slots 58 and 62, down the opposed sides of the container, through the grooves 71 and 72, and along the bottom of the container. In FIG. 4, the container 12 is similarly hung except that the strap 14 extends through grooves 60 and 64. The device may also be hung with the strap extending through slots 58 and 64 or through 60 and 62.

Figure 5:
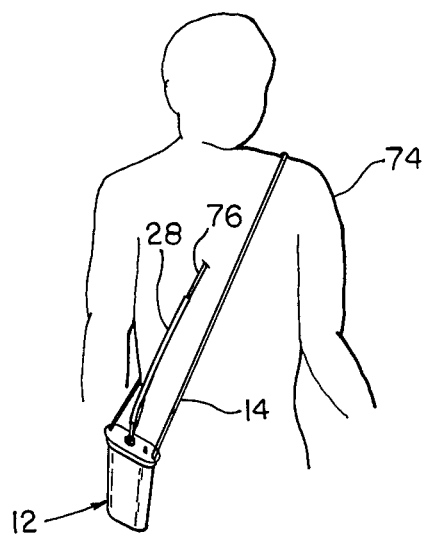
FIG. 5 is an illustration of the drainage device of FIG. 1 on a reduced scale and with the device being supported by an ambulatory patient.

FIG. 5 illustrates the use of the drainage device 12 and strap 14 arranged to be carried from the shoulder of a patient 74 such as in the case of an ambulatory patient. In this strap adjustment or arrangement, the full length of the strap is extended from its ends and utilized to support the container 12. Tube 28 is shown connected to a catheter 76 disposed in the pleural cavity of the patient.

Figure 6:
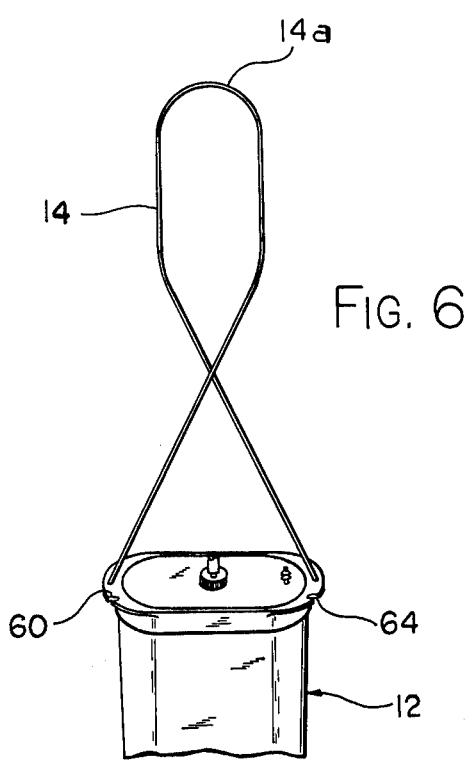
FIG. 6 is a perspective view of the drainage device of FIG. 1 on a reduced scale with the strap in a transitory position preparatory to connecting the strap in the final position shown in FIG. 7.
Figure 7:
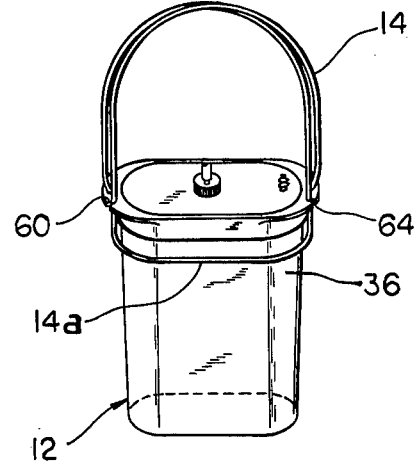
FIG. 7 is a perspective view of the drainage device of FIG. 1 on a reduced scale with the strap in a modified arrangement which provides the drainage device with a looped handle.

FIGS. 6 and 7 show another manner of employing the strap 14. In this strap adjustment, the strap 14 is first looped as in FIG. 6, and the upper end portion indicated at 14a is then moved down over one side of the container and the strap inserted, for example, in the front two grooves 60 and 64 and such that the upper end portion 14a extends around a part of the upper portion 36 of the container. In the supporting arrangement shown in FIG. 7, the strap provides a handle or hand strap that can be hand-held for transferring the container.

The strap 14 can be utilized in still further arrangements not illustrated. For example, instead of looping the strap around the upper portion of the container, as shown in FIG. 7, the strap end portion 14a could be looped around the bottom of the container so that it passes through openings 71 amd 72 to thereby provide a hand strap similar to that of FIG. 7 but which is shorter in length. These strap arrangements provide for various amounts of strap take-up and without producing a dangling strap portion.

The container 12 and chamber 24 are preferably formed of a relatively rigid or hard transparent plastic material, for example, a relatively hard transparent butadiene styrene, acetate butyrate styrene or the like. By forming the container 12 and chamber 24 from plastic, the device is relatively light even where the drainage container includes a collection chamber and a liquid seal chamber, and it is readily adapted to be supported in various manners, such as those shown herein. The strap 14 is preferably formed from a relatively flexible, soft plastic such as polyvinyl chloride.

The strap 14 is longer than the maximum peripheral distance around the container 12. The strap is preferably sufficiently long to support the container at the hip from the shoulder of the person intending to use the drainage device.

In view of the above, it will be seen that the several objects and advantages of the invention are achieved and other advantageous results obtained. As various changes could be made in the above construction without departing from the scope of the invention, it is intended that all matter contained in the above description and shown in the accompanying drawings shall be interpreted as illustrative and not in a limiting sense.

What is claimed is:

1. A medical drainage device comprising a container for receiving body fluid drainage from a patient, said container including fluid inlet means adapted for fluid communication with a source of body fluid drainage, an upper portion having two opposed sides with at least one groove in each of said opposed sides extending laterally inwardly from the outer periphery of said container, and a flexible strap, means for connecting opposite ends of said strap to said upper portion respectively adjacent said opposed sides, said strap connecting means being spaced from said grooves, said strap and each of said grooves being sized relative to each other to permit movement of selected portions of said strap into said grooves to provide a selected strap arrangement capable of supporting said container.

2. The device of claim 1 wherein each of said grooves includes a hole sized to receive said strap and an entrance slot extending from the hole to the periphery of said container adjacent said hole to allow insertion of said strap, side wall first, through said entrance slot and into said hole.

3. The device of claim 2 wherein each of said holes and said slots are sized slightly smaller in width than the width of said strap.

4. The device of claim 3 wherein each of said slots has a portion with a width smaller than the width of each of said holes.

5. The device of claim 4 wherein the length of said strap is greater than the maximum peripheral distance around said container.

6. The device of claim 5 wherein each of said opposed sides has another groove similar to said one groove.

7. The device of claim 1 wherein said container is of plastic material.

8. The device of claim 1 wherein said container comprises a lid closing the upper end thereof, a liquid seal chamber, and a body fluid collection chamber below said seal chamber, and fluid connection means adapted for connection with a body cavity extending through said lid and into said seal chamber, said seal chamber being in fluid communication with said collection chamber.

9. The device of claim 1 wherein said container is formed of substantially rigid plastic, and said strap is formed of a plastic which is more flexible than that of said container.

10. The device of claim 1 wherein said container has a lower end portion with a peripheral skirt extending below the bottom of said container, said skirt having a slot in said skirt at each side of said container for receiving said strap to permit said strap to extend along the bottom of said container substantially without extending below the bottom of said skirt.

11. The device of claim 10 wherein said strap is longer than the maximum periphery around said container and is formed of plastic.

12. The device of claim 11 wherein said strap is capable of being simultaneously disposed in each of said grooves and each of said skirt slots and having a portion extending above said upper portion of said container for supporting said container from a support above said container.

13. The device of claim 11 wherein said strap is sufficienhy long to support said container at the hip from a shoulder of an average sized adult person.

14. A medical drainage device comprising a container for receiving body fluid drainage from a patient, said container including fluid inlet means adapted for fluid communication with a source of body fluid drainage, an upper portion having a laterally outwardly extending flange at each of two opposite sides thereof, each of said flanges having at least one groove extending laterally inwardly from the outer periphery of the flange, and a flexible strap having opposite ends connected to said upper portion respectively adjacent said opposite sides and at points spaced from said grooves, said strap and each of said grooves being sized relative to each other to permit laterally inward movement of said strap, side wall first, into said grooves to provide selected strap arrangements capable of supporting said container in different ways, the width of said grooves being less than the width of said strap so that outward lateral movement of said strap in said groove is opposed by frictional engagement between the opposed side walls of said grooves and said strap.

15. The device of claim 14 wherein said container has a lower end portion with a peripheral skirt extending below the bottom of said container, said skirt having a slot at each side of said container for receiving said strap to permit said strap to extend along the bottom of the container substantially without extending below the bottom of said skirt.

16. The device of claim 15 wherein each of said grooves includes a hole sized to receive said strap and an entrance slot extending from the hole to the periphery of the flange to allow insertion of said strap, side wall first, through the entrance slot and into the hole.

17. The device of claim 15 wherein the medical drainage device is a thoracic drainage device, said container includes a bottom wall closing the bottom end and a lid closing the upper end, tube means extending through said lid and into said container, said tube means having means externally of said container for connecting fluid coupling means thereto which is adapted for connection with the pleural cavity of a patient.

18. The device of claim 17 wherein said container comprises a liquid seal chamber, and a body fluid collection chamber below said seal chamber, and, said seal chamber being in fluid communication with said collection chamber.

19. The device of claim 17 wherein said container is formed of a relatively hard plastic material, said strap is formed of a relatively flexible plastic material, and the opposite ends of said strap are respectively connected to said flanges.

20. The device of claim 14 wherein said strap is circular in cross-section and is of plastic material.

21. The device of claim 14 wherein each of said grooves includes a hole sized to receive said strap and an entrance slot extending from the hole to the periphery of the flange to allow insertion of said strap, side wall first, through the entrance slot and into the hole.

* * * * *